United States Patent [19]

King

[11] Patent Number: 4,697,080
[45] Date of Patent: Sep. 29, 1987

[54] ANALYSIS WITH ELECTRON MICROSCOPE OF MULTIELEMENT SAMPLES USING PURE ELEMENT STANDARDS

[75] Inventor: Wayne E. King, Western Springs, Ill.

[73] Assignee: The United States of America as represented by the United States Department of Energy, Washington, D.C.

[21] Appl. No.: 818,308

[22] Filed: Jan. 6, 1986

[51] Int. Cl.$^4$ .................. G01N 23/225; G01N 23/223
[52] U.S. Cl. ............................. 250/307; 250/310; 250/397; 378/45; 378/46; 378/48
[58] Field of Search ............... 250/310, 397, 307; 378/48, 46, 45; 364/498

[56] References Cited

U.S. PATENT DOCUMENTS

| | | | |
|---|---|---|---|
| 2,418,029 | 3/1947 | Hillier | 250/310 |
| 3,146,347 | 8/1964 | Ziegler | 250/310 |
| 3,204,095 | 8/1965 | Watanabe | 250/310 |
| 3,612,861 | 10/1971 | Dorfler | 250/310 |
| 3,694,635 | 9/1972 | Hoetzel | 250/310 |
| 4,037,101 | 7/1977 | Okumura et al. | 250/310 |
| 4,288,692 | 9/1981 | Schamber et al. | 250/310 |
| 4,355,232 | 10/1982 | Todokoro et al. | 250/310 |
| 4,357,536 | 11/1982 | Varma et al. | 250/397 |

OTHER PUBLICATIONS

Allen, Philosophical Magazine A, 1981, vol. 43, No. 2, 325–335.
Philibert et al., J. Phys. D. Appl. Phys., vol. 11, No. 3, Nov. 1970, pp. L70–L72.

Primary Examiner—Craig E. Church
Assistant Examiner—Jack I. Berman
Attorney, Agent, or Firm—William Lohff; Michael J. Higgins; Judson R. Hightower

[57] ABSTRACT

A method and modified analytical electron microscope for determining the concentration of elements in a multielement sample by exposing samples with differing thicknesses for each element to a beam of electrons, simultaneously measuring the electron dosage and x-ray intensities for each sample of element to determine a "$K_{AB}$" value to be used in the equation $$\frac{I_A}{I_B} = K_{AB} \frac{C_A}{C_B}$$

where I is intensity and C is concentration for elements A and B, and exposing the multielement sample to determine the concentrations of the elements in the sample.

3 Claims, 1 Drawing Figure

ANALYSIS WITH ELECTRON MICROSCOPE OF MULTIELEMENT SAMPLES USING PURE ELEMENT STANDARDS

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

This invention relates to analytical electron microscopy and more particularly to an analytical method and associated apparatus involving an analytical electron microscope for determining the composition of a sample containing two or more elements.

Previous use of analytical electron microscopes to determine the elemental composition of samples has involved the use of measured x-ray intensities in a technique identified as x-ray energy dispersive spectroscopy. The fundamental difficulty in applying this technique is the determination of the proportionality constant relating sample composition to measured x-ray intensity. As background, the number of x-ray photons detected per incident electron in a pure element sample is given by $$I/\phi = \left[ \frac{Q\omega a\epsilon \frac{\Omega}{4\pi}}{A} \right] \rho N_o t$$

where I is the number of detected x-ray photons, $\phi$ is the total electron dose during the x-ray detector live time, Q is the ionization cross section, $\omega$ is the fluorescence yield, $a$ is the x-ray partition function, $\epsilon$ is the detector efficiency, $\Omega/4\pi$ is the fractional solid angle subtended by the x-ray detector, A is the sample atomic weight, $\rho$ is the sample density, $N_o$ is Avagadro's number, and t is the sample thickness. The elemental composition of a two element sample can be determined using the ratio method.

$$\frac{C_A}{C_B} = K_{AB} \frac{I_A}{I_B}$$

where $K_{AB}$ is a "K" factor equal to $$K_{AB} = \frac{\left[ \frac{Q\omega a\epsilon}{A} \right]_B}{\left[ \frac{Q\omega a\epsilon}{A} \right]_A}$$

and $C_A$ and $C_B$ are concentrations of elements A and B, respectively, in weight percent. The above calculations are applied for all components with the remaining relationship being that the total concentration equals 100%. In many instances, the factor $K_{AB}$ has been previously determined by experimental measurements on well characterized multi-element standards when conditions permit the preparation of the standard with known concentrations. However, the multi-element standard technique has some problems in that it may be difficult to prepare the multi-element standard particularly where the elements do not readily form alloys.

Accordingly, one object of the invention is a method of determining the concentration of elements in a sample by analytical electron microscopy. Another object of the invention is a method which does not require the preparation and use of multielement standards. These and other objects will become apparent from the following detailed description.

SUMMARY OF THE INVENTION

Briefly, this invention is directed to a method and modified analytical instrument for determining the concentrations of elements in a multielement sample without the need to prepare alloy or other multielement samples of those elements in known concentrations. The method utilizes the steps of exposing pure element samples of different thicknesses for each element to a beam of electrons in an analytical electron microscope, measuring the electron dosage and x-ray intensities for each sample of element to determine a "$K_{AB}$" value to be use in the equation $$\frac{I_A}{I_B} = K_{AB} \frac{C_A}{C_B}$$

where 1 is intensity and C is concentration for elements A and B, exposing the multielement sample to the electron beam, and measuring the characteristic x-ray intensities for each of the elements in a multielement unknown sample to determine the concentration of elements.

The electron microscope used for this method is modified to include an electrically isolated condenser aperture between the electron gun and sample, a movable sample support, an electron collector (illustrated by a Faraday cup) below the sample support, and measuring means connected to the condenser aperture and Faraday cup for the simultaneous measurement of electron dosage and x-ray intensity for each of the one element samples.

With new multicomponent samples having elements whose "K" values have been previously determined, it may not be necessary to determine new "K" values for each sample. However, since parameters of the electron microscope associated with expressions in the basic equation may change with time, it is usually advisable to carry out the tests with single component samples following a reasonable period such as 3–4 months.

DETAILED DESCRIPTION OF THE PREFERRED EMBODIMENT

Figure 1:
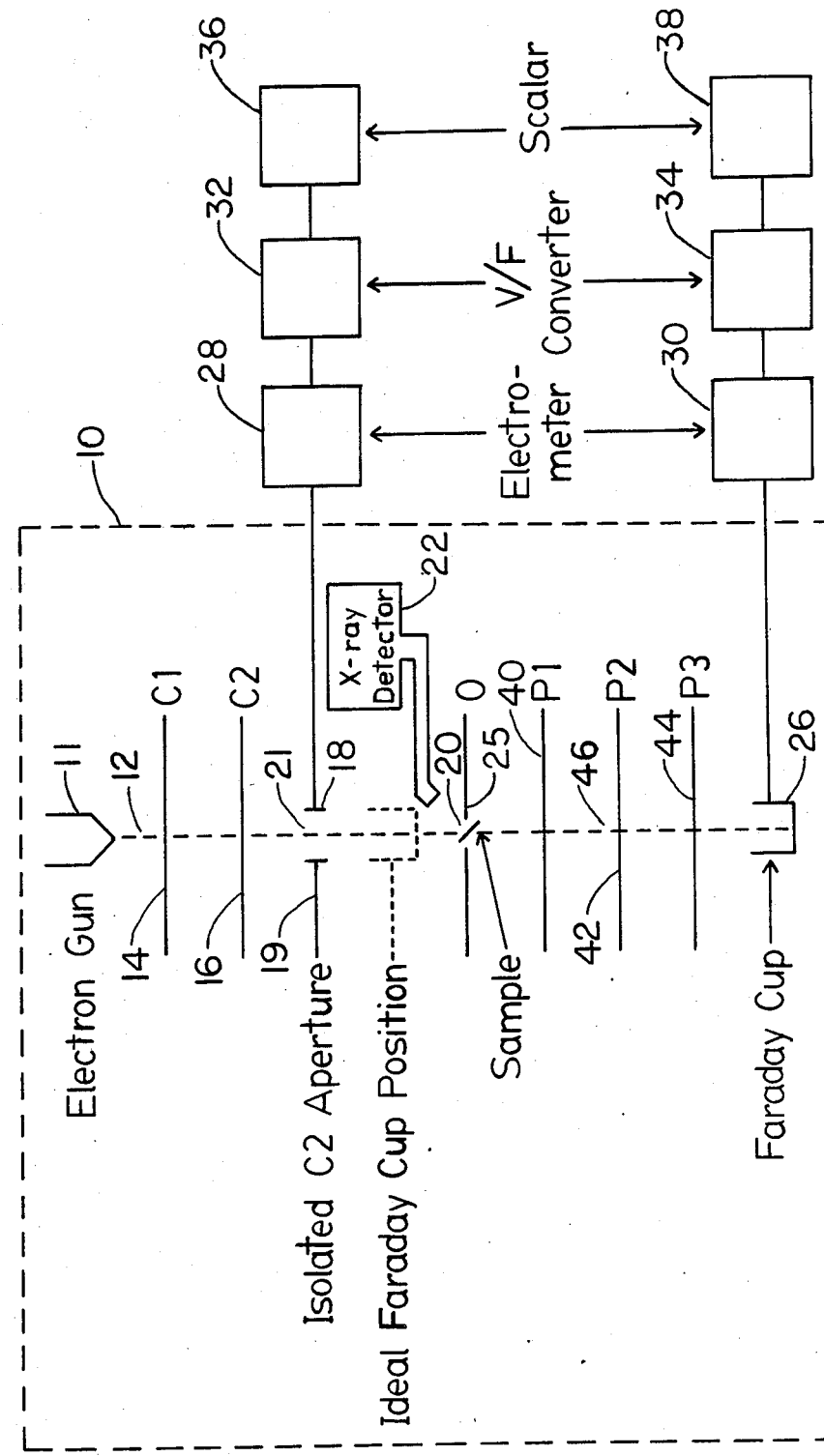
FIG. 1 is schematic of the modified electron microscope as one embodiment of the invention.

In the invention, a method is used to determine the concentration of at least two elemental components in a sample containing a plurality of elemental components comprising the steps of exposing elemental samples of pure component with at least two different thicknesses for each of the components to an electron beam in an analytical electron microscope to generate an x-ray intensity, measuring the electron dose for each thickness of each elemental sample of each component, determining the mathematical relationship of $I/\phi$ for each elemental sample where I is x-ray intensity and $\phi$ is electron dose at each of the thicknesses, determining a linear relationship between the $I/\phi$ values for each component over a range of thicknesses with the slope of the linear relationship equal being equal to $$\left[\frac{Q\omega a\epsilon \frac{\Omega}{4\pi}}{A}\right]\rho N_o.$$

The factor $K_{AB}$ in the equation $$\frac{I_A}{I_B} = K_{AB}\frac{C_A}{C_B}$$

where I is the x-ray intensity and C is the concentration for components A and B can be calculated from the ratio of the slopes for element A, $S_A$, and element B, $S_B$ $$K_{AB} = \frac{S_B}{S_a} \frac{\rho_A}{\rho_B}$$

where "$S_B$" and "$S_A$" are the slopes for elements B and A, respectively and $\rho_A$ and $\rho_B$ are the densities. The subsequent step involves exposing the multicomponent sample to an electron beam in an analytical electron microscope and determining the x-ray intensities for each of the components to determine their relative concentration.

The electron microscope 10 of FIG. 1 includes modifications necessary in carrying out the measurements. As illustrated, electron gun 11 is used to generate an electron beam 12 which is concentrated by lens elements 14 and 16 and passed through aperture 18 to sample 20 which is set at an angle for x-ray detection. X-ray photons are generated by the interaction of the electron beam 12 with sample 20 with a small hole formed in preparation to facilitate an unobstructed path between aperture 18 and electron collector 26 and measured by an x-ray detector 22. The electron dose at the sample 20 is measured by first relating the electron current intercepted by the frame 19 of aperture 18 to total transmitted beam current at an electron collector illustrated by Faraday cup 26 when the beam path 46 between the aperture 18 and the Faraday cup 26 is unobstructed. With sample 20 in place, the current intercepted by the frame 19 of aperture 18 is integrated during acquisition of the x-ray spectrum. The electron dose is calculated using the dose at aperture 18 and the relationship between the electron current at aperture 18 and the total transmitted beam current at the Faraday cup 26 when the beam path between aperture 18 and Faraday cup 26 is unobstructed. The electrometers 28 and 30, V/F converters 32 and 34 and scalar 36 and 38 comprise beam current integrators used to measure electron dose. V/F converters 32 and 34 convert the electron current to pulses which are counted by scalars 36 and 38 as a measure of the number of electrons striking the sample. Imaging lens 40, 42 and 44 provide focusing of the beam at the Faraday cup 26.

With measurements of x-ray intensity and electron dose for each elemental sample at each of at least two thicknesses, a table or a linear plot of the values for $I/\phi$ for each component may be provided to cover a range of thickness. As these plots are compared to form a linear relationship between $I/\phi$ for each component over the range of thicknesses, the slope of the linear relationship may be determined. Values of $K_{AB}$ where A and B are the separate elements A and B are calculated from the ratio of slopes for element A, $S_A$, and element B, $S_B$ $$K_{AB} = \frac{S_B}{S_a} \frac{\rho_A}{\rho_B}$$

In the next step, the multicomponent sample is exposed to the electron gun and measurements of each intensity are made. Determinations of the relative concentrations $C_A$ and $C_B$ are then made from the equation $$\frac{I_A}{I_B} = K_{AB}\frac{C_A}{C_B}$$

with absolute concentrations being available from the relative concentrations for all of the components in a sample with the total equaling 100 percent by weight. As described above and illustrated in FIG. 1, the electron microscope 10 comprises an electron gun 11 and at least one condensing lens 14 for directing a beam 12 of electrons in a path 46 towards a sample, a sample support disposed in the path separated from the condensing lens and movable laterally to provide an unobstructed path for the electron beam, an electrically isolated condenser aperture 18 having a frame 19 and an opening 21 as the aperture positioned in the path between the condensing lens and the sample support, at least one imaging lens 40 in the path beyond the sample support, a Faraday cup 26 in the path beyond the imaging lens 40, and electron measuring means connected to the frame of the electrically isolated condenser aperture and the Faraday cup for separately measuring the quantity of electrons striking the aperture frame and Faraday cup.

Preferably, the electron measuring means as illustrated by electrometers 28 and 30, V/F converters 32 and 34 and scalar 36 and 38 operate to provide a measurement simultaneously of the electrons striking the aperture frame and the Faraday cup. This method may be used with samples having a variety of components including Si, Al, Fe, Cu and other elements having characteristic x-rays in the energy range 0.5-20 keV.

As a demonstration of the invention, an electron microscope was modified with the features illustrated in FIG. 1. X-ray production rates, $I/\phi$, were measured as a function of sample thickness in samples of Al, Si, Fe and Cu. Measured values of $K_{ASi}$ and those calculated based on theory are provided in Table I below.

In the modification of the electron microscope, an electron Faraday cup was constructed for the Philips EM400T electron microscope and installed in the 35 mm camera port. The Faraday cup is comprised of an inner Cu cup and an outer Ta shield. For the Faraday cup, the outer and inner cups were made of Ta and Cu, respectively. The outer cup had a thickness in the order of 1 mm to stop electrons from penetrating through the cup. For the inner cup, the thickness of the closed end or bottom was in the order of 3-5 mm to also prevent electrons from penetrating through the cup. A ratio of length to diameter for the inner cup was also at a value above 5 to reduce secondary electron emission. The electron current measured by this cup is within 1% of that measured by a well characterized cup. An electrically isolated condenser aperture mechanism available commercially was fitted with thick Pt apertures and installed in place of the standard condenser aperture mechanism. The electron currents intercepted by the Faraday cup and aperture were integrated by two Keithley 602 electrometers coupled with a pair of voltage-to-frequency converters and two Otec 776 scalars. This instrumentation is necessary for integration of the very low beam currents in the analytical electron microscope ($5 \times 10^{-11}$ A) The integration circuit was calibrated using a Keithley 261 current source such that the accuracy of the dose measurement was limited by the accuracy of the Faraday cup and its associated electrometer.

Electron optically thin, 3 mm diameter pure element standards (Al, Si, Fe and Cu) were mounted in a double tilt Be sample holder. The sample was loaded into the analytical electron microscope with LaB$_6$ filament operating at 120 keV. The region of the sample used for microanalysis was selected such that the absorption path length was minimized. The sample was tilted toward the x-ray detector by 35° and an exact two-beam diffraction condition was established. Convergent beam electron diffraction (CBED) patterns and sample tilts were recorded. The sample was tilted away from the strong diffracting condition without losing the electron beam position. An x-ray spectrum was then recorded for 200 seconds live time by an EDAX X-ray detector interfaced to a Nuclear Data 66 multichannel analyzer. X-ray count rates were always kept below 1200 counts per second so that effects of pulse pileup were negligible. The fraction of the total beam current intercepted by the isolated condenser aperture was integrated during accumulation of the x-ray spectra. Without changing illumination conditions, the electron beam was moved off of the sample to the hole in order to provide an unobstructed path from the codenser aperture to the Faraday cup. Five 10 second integrations of the currents intercepted by the condenser aperture and Faraday cup were carried out and the results were recorded. In 10 second $> 2 \times 10^{10}$ electrons were collected in the Faraday cup. The procedure was repeated for two additional sample thicknesses after which the so-called "hole count" was accumulated. During accumulation of the hole count, the condenser aperture and Faraday cup currents were integrated as a check on the previous 10 second measurements.

The operating reflections for the CBED patterns were indexed. The technique described by Samuel M. Allen, Philosophical Magazine, A43, P. 325 (1981) was employed to deduce the sample thickness. Measured thicknesses were corrected for the change in sample tilt between CBED and x-ray measurements. The resultant accuracy in t was ±2%.

The hole count was subtracted from the experimental spectra. Regions of interest were selected surrounding the K x-ray lines. Peaks and background were fit simultaneously using an unconstrained, nonliner, least squares fitting procedure. The background was fitted with a cubic polynomial and the peaks were fitted with Gaussian-shaped curves with peak position, amplitude, and width included as free parameters.

Electron doses at the conenser aperture integrated during accumulation of x-ray sectra were multiplied by the ratio of the current intercepted by the Faraday cup to that intercepted by the condenser aperture and by the live time to real time ratio to obtain the total electron dose delivered to the sample during accumulation of the spectra.

For each sample, the effective x-ray production rate $I/\phi$ was plotted as a function of thickness. In the thin samples used in this study, <2000 Å, absorption and fluorescence effects are negligible and, $I/\phi$ vs t is a linear function. Any data nor fitting a straight line with zero intercept was assumed to result from the x-ray measurement not being carried out at the same point where the thickness was measured and was therefore rejected. To reduce random errors, the data was fit to a straight line. From the slope of this line, the x-ray production and detection efficiencies were determined and the K factor normalized to Si, K$_{ASi}$, was calculated.

The ratio of currents between the condenser aperture and the Faraday cup depends on filament excitation, C1 excitation, C2 excitation, and condenser aperture size. Therefore the ratio must be measured immediately before or after accumulation of an x-ray spectra under the same illumination conditions. In this experiment, it was important that the ratio be independent of fluctuations in the beam current. The ratio was found to be invariant over 60 seconds to 0.02% whereas the electron beam current from the LaB$_6$ filament varied on the average 1% over 60 seconds. Thus, the electron dose determined from the dose measured at the condenser aperture multiplied by the ratio of the current in the Faraday cup to the current at the aperture is accurate to ±2% assuming that the filament emission does not fluctuate by more than ±1%.

TABLE I

SUMMARY OF RESULTS

| Element | t (Å) | $I/\phi$ (photons/electron) | Slope (photons/electron/cm) | $Q\omega a \epsilon \frac{\Omega}{4\pi} / A$ (cm$^2$/g/mole) | K$_{ASi}$ (measured) | K$_{ASi}$ (theoretical) |
|---|---|---|---|---|---|---|
| Si | 427 ± 12 | 1.11 × 10$^{-7}$ | 2.64 × 10$^{-2}$ | 5.29 × 10$^{-25}$ | 1.00 ± 0.00 | 1.00 |
|  | 916 ± 35 | 2.14 × 10$^{-7}$ |  |  |  |  |
|  | 1517 ± 10 | 4.43 × 10$^{-7}$ |  |  |  |  |
| Al | 581 ± 11 | 1.54 × 10$^{-7}$ | 2.64 × 10$^{-2}$ | 4.39 × 10$^{-25}$ | 1.16 ± 0.07 | 1.02 |
|  | 899 ± 10 | 2.48 × 10$^{-7}$ |  |  |  |  |
|  | 1052 ± 35 | 2.66 × 10$^{-7}$ |  |  |  |  |
|  | 1767 ± 40 | 4.68 × 10$^{-7}$ |  |  |  |  |
| Fe | 996 ± 4 | 5.44 × 10$^{-7}$ | 5.69 × 10$^{-2}$ | 6.72 × 10$^{-26}$ | 1.57 ± 0.09 | 1.45 |
|  | 1653 ± 86 | 9.44 × 10$^{-7}$ |  |  |  |  |
| Cu | 543 ± 23 | 3.34 × 10$^{-7}$ | 5.97 × 10$^{-2}$ | 7.03 × 10$^{-27}$ | 1.70 ± 0.10 | 1.70 |
|  | 603 ± 8 | 3.23 × 10$^{-7}$ |  |  |  |  |
|  | 1436 ± 56 | 8.55 × 10$^{-7}$ |  |  |  |  |

By convention, values K$_{AB}$ are referenced to Si, thus B is Si. A summary of all results is given in Table I above. The values of K$_{ASi}$ apply to the EDAX Si(Li) x-ray detector used in this study. Calculated values for K$_{ASi}$ are based on ionization cross sections calculated from the Bethe theory. The uncertainty in measured K$_{ASi}$ are 6% (resulting from uncertainties in thickness and dose measurement) whereas the uncertainty in calculated values is expected to be substantially larger due to uncertainties in calculation of each parameter. Theory and experiment agree reasonably well at all photon energies. Measurement of $I/\phi$ vs t reduces errors in measured x-ray production rate due to the presence of amorphous or oxide layers which may coat the sample surface of the pure element standard The embodiments of the invention in which an exclusive property or privilege is claimed are defined as follows:

1. A method of determining the composition of a multielement sample containing a plurality of predetermined elemental components comprising the steps of
   providing single component samples of each component having at least two thicknesses,
   directing a beam of electrons at each sample to generate characteristic x-ray intensities,
   simultaneously measuring the x-ray intensities (I) and beam dosage ($\phi$) associated with said beam of electrons,
   determining a K factor by $$\frac{S_B}{S_A} \frac{\rho_A}{\rho_B}$$

where "$S_B$" and "$S_A$" are the slopes of curves of $I/\phi$ versus thickness determined from said single component samples at said thicknesses and $\rho A$ and $\rho B$ are the densities for components A and B, the $K_{AB}$ factor being a constant in the equation $$\frac{C_A}{C_B} = K_{AB} \frac{I_A}{I_B}$$

where I is intensity and C is concentration,
   exposing the multicomponent sample to the beam of electrons to generate characteristic x-ray intensities for each component,
   and measuring the individual intensities to determine the relative concentration of each in the above equation.

2. The method of claim 1 wherein the step of measuring the beam current for each single component sample is carried out by measuring the quantity of electrons in the beam that are blocked from reaching the sample and by a predetermined ratio of blocked to unblocked electrons, determining the quantity of electrons reaching the sample 3. The method of claim 2 wherein the step of measuring the quantity of electrons is determined by integrating the changing quantity of electrons over a predetermined time.

* * * * *